United States Patent [19]
Kim et al.

[11] Patent Number: 6,072,056
[45] Date of Patent: Jun. 6, 2000

[54] METHOD OF PREPARING WATER FREE ISOTHIAZOLONE

[75] Inventors: Seung-Hwan Kim; Jeong-Ho Park; Jin-Man Kim; Ki-Seung Choi; Myung-Ho Cho, all of Kyungki-do; Soon-Jong Hahn, Seoul, all of Rep. of Korea

[73] Assignee: SK Chemical, Rep. of Korea

[21] Appl. No.: 09/098,108

[22] Filed: Jun. 16, 1998

[30] Foreign Application Priority Data

Jun. 17, 1997 [KR] Rep. of Korea ............. 97-25185
Jul. 10, 1997 [KR] Rep. of Korea ............. 97-31944

[51] Int. Cl.[7] .................................................. C07D 275/03
[52] U.S. Cl. .................................................. 548/213
[58] Field of Search ............................. 548/213

[56] References Cited

U.S. PATENT DOCUMENTS

| | | | |
|---|---|---|---|
| 3,870,795 | 3/1975 | Miller et al. | 424/270 |
| 4,067,878 | 1/1978 | Miller et al. | 260/302 |
| 5,068,344 | 11/1991 | Petigara et al. | 548/213 |
| 5,466,818 | 11/1995 | Petigara et al. | 548/213 |

*Primary Examiner*—Laura L. Stockton
*Attorney, Agent, or Firm*—Gifford, Krass, Groh, Sprinkle, Anderson & Citkowski, P.C.

[57] ABSTRACT

A method of preparing water free isothiazolone having the steps of obtaining an extract from an aqueous solution containing isothiazolone by using a halogenationed hydrocarbon or nitrated hydrocarbon, removing the halogenationed hydrocarbon or nitrated hydrocarbon from the extract, and adding a organic solvent such as glycol, alcohol and glycol ether provides a water free isothiazolone having a high stability without forming wastes and harmful gas.

13 Claims, No Drawings

METHOD OF PREPARING WATER FREE ISOTHIAZOLONE

CROSS REFERENCE TO RELATED APPLICATION

This application is based on application No. 97-25185 and No. 97-31944 filed in the Korea Industrial Property Office on Jun. 17, 1997 and Jul. 10, 1997 respectively, the content of which are incorporated hereinto by references.

BACKGROUND OF THE INVENTION (a) Field of the Invention

The present invention relates to a method of preparing water free isothiazolone, more particularly, to a method of preparing water free isothiazolone having a relatively high stability and a method of preparing substantially pure water free 5-chloro-2-methyl-3-isothiazolone having a relatively high antibacterial activity.

(b) Description of the Related Art

Isothiazolones of formula 1 are well known as microbicides and are employed in many industrial and household systems.

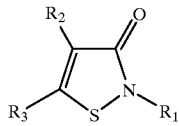

[formula 1]

wherein

R1 is selected from the group consisting of hydrogen; unsubstituted or halogen- or hydroxy-substituted $(C_1-C_{10})$ alkyl; unsubstituted or halogen-substituted $(C_2-C_{10})$ alkenyl; unsubstituted or halogen-substituted $(C_2-C_{10})$ alkynyl; halogen atom; unsubstituted or $(C_1-C_{10})$ alkyl- or $(C_2-C_9)$ alkoxy-substituted aralkyl, and R2 and R3 are the same or different and selected from the group consisting of hydrogen, halogen and $(C_1-C_4)$ alkyl respectively.

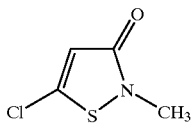

[formula 2]

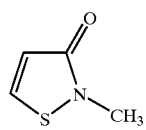

[formula 3]

Among then, 5-chloro-2-methyl-3-isothiazolone of formula 2 has a relatively high antibacterial activity compared to 2-methyl-3-isothiazolone. Therefore, a method of preparing pure 5-chloro-2-methyl-3-isothiazolone is required.

Isothiazolone have a very low stability in a practical condition required a long time storage. A lot of method to improve a stability of isothiazolone have been developed.

U.S. Pat. No. 3,870,595 and U.S. Pat. No. 4,067,878 disclose an isothiazolone stabilization method adding a metal nitrite salt or metal nitrite salt to prevent a chemical decomposition. In certain applications, e.g., preservation of latex emulsion, these metal stabilization salts cause problems which can reduce the performance or value of such systems. Another problem with such metal stabilization salts is that they cause corrosion in certain systems. For example, chloride salts have a corrosive effect on many metals.

U.S. Pat. No. 5,068,344 discloses a process for the preparation of salt free, water free 3-isothiazolone compounds by using an ammonia. This method requires a separating step. In the separating step, 10–20 wt % of total isothiazolone is not separated from the filtered ammonium chloride salt. These cause a lot of wastes. Also, the ammonium chloride, that is not separated from isothiazolone, is accompanied with a final product and give a bad effect on a its stability.

U.S. Pat. No. 5,466,818 discloses a method of producing substantially separated 5-chloro-2-methyl-3-isothiazolone and 2-methyl-3-isothiazolone from a mixture of their hydrochloride salts. This method has a harmful working condition because of hydrogen chloride gas formation. Also, a stability of isothiazolone may decrease because of heating step. This method requires a filtering step to isolate isothiazolone from isothiazolone hydrochloride salt.

SUMMARY OF THE INVENTION

It is an object of the present invention to provide a method of preparing water free isothiazolone of high stability without forming wastes and a harmful gas.

It is another object to provide a method of preparing substantially pure water free 5-chloro-2-methyl-3-isothiazolone having a high antibacterial activity.

In order to achieve these objects, the present invention provides a method of preparing water free isothiazolone comprising the steps of obtaining an extract from an aqueous solution containing isothiazolone by using a halogenationed hydrocarbon or nitrated hydrocarbon, and removing the halogenationed hydrocarbon or nitrated hydrocarbon from the extract.

Also, the present invention provides a method of preparing substantially pure water free 5-chloro-2-methyl-3-isothiazolone comprising the steps of obtaining an extract from an aqueous solution containing 5-chloro-2-methyl-3-isothiazolone by using a halogenationed hydrocarbon or nitrated hydrocarbon, washing the extract out with water, and removing the halogenationed hydrocarbon or nitrated hydrocarbon from the extract.

DETAILED DESCRIPTION OF THE PREFERRED EMBODIMENTS

In 1975, V. Gutmann et al. studied unshared electron pair acceptances of various organic solvents. An organic solvent having a relatively high unshared electron pair acceptance can be mixed with water well and have a high boiling point. Although halogenationed hydrocarbon and nitrated hydrocarbon have high unshared electron pair acceptances, they have low water-solubilities and boiling points. Therefore, a salt free water free isothiazolone can be prepared by obtaining an extract from an aqueous solution containing isothiazolone by using halogenationed hydrocarbon or nitrated hydrocarbon, and removing the halogenationed hydrocarbon or nitrated hydrocarbon from the extract. A water free isothiazolone solution can be prepared by adding an organic solvent such as glycol, alcohol and glycol ether to the salt free water free isothiazolone. The halogenationed hydrocarbon or nitrated hydrocarbon can be recycled without an additional separating or filtering step. Moreover, a working condition is mild because of using an aqueous solution. This method does not cause wastes by reusing isothiazolone contained a separated aqueous solution.

It is preferable that the aqueous solution containing isothiazolone is an aqueous solution having a mixture of 5-chloro-2-methyl-3-isothiazolone and 2-methyl-3-isothiazolone. A ratio of 5-chloro-2-methyl-3-isothiazolone and 2-methyl-3-isothiazolone is preferably to be 10:90–99.99:0.01.

The halogenationed hydrocarbon can be methylene chloride, chloroform, carbon tetrachloride, ethylene chloride or dichloroethane and the nitrated hydrocarbon can be nitromethane or nitroethane.

It is preferable that the organic solvent can dissolve and stabilize isothiazolone. A solvent having a hydroxy group such as glycol, alcohol and glycol ether can be used as the organic solvent. In certain system, an aliphatic or aromatic hydrocarbon can be used as the organic solvent. The organic solvent is preferably to ethylene glycol, propylene glycol, dipropylene glycol, ethylene glycol monomethyl ether or ethylene glycol dimethyl ether. Table 1 shows a ratio of the organic solvent and isothiazolone.

TABLE 1

| itsothiazolone | 0.00001–99 wt % |
|---|---|
| organic solvent | 1–99.99999 wt % |

5-chloro-2-methyl-3-isothiazolone has a relatively high antibacterial activity compared to 2-methyl-3-isothiazolone. Therefore, a method of preparing pure 5-chloro-2-methyl-3-isothiazolone may be required.

Both 5-chloro-2-methyl-3-isothiazolone and 2-methyl-3-isothiazolone can be dissolved in an acidic aqueous solution well. They have different basicities and both basicities are very low. 5-chloro-2-methyl-3-isothiazolone and 2-methyl-3-isothiazolone can be extracted selectively by using an organic solvent, which is immiscible with water.

A free base isothiazolone can be prepared by obtaining an extract from an aqueous solution containing 5-chloro-2-methyl-3-isothiazolone by using a halogenationed hydrocarbon or nitrated hydrocarbon and removing the halogenationed hydrocarbon or nitrated hydrocarbon from the extract. At this time, basicity difference between 5-chloro-2-methyl-3-isothiazolone and 2-methyl-3-isothiazolone causes different distributions between a water layer and an organic layer of a halogenationed hydrocarbon or nitrated hydrocarbon. Accordingly, substantially pure free base 5-chloro-2-methyl-3-isothiazolone can be prepared by obtaining an extract from an aqueous solution containing 5-chloro-2-methyl-3-isothiazolone by using a halogenationed hydrocarbon or nitrated hydrocarbon, washing the extract out with water, and evaporating the halogenationed hydrocarbon or nitrated hydrocarbon from the extract. Substantially pure 5-chloro-2-methyl-3-isothiazolone hydrochloride salt can be prepared by obtaining an extract from an aqueous solution containing 5-chloro-2-methyl-3-isothiazolone by using the halogenationed hydrocarbon or nitrated hydrocarbon, washing the extract out with water, adding hydrogen chloride gas to the extract, and filtering solids formed by the hydrogen chloride gas adding step.

Also, substantially pure 5-chloro-2-methyl-3-isothiazolone solution can be prepared by adding an organic solvent to substantially pure 5-chloro-2-methyl-3-isothiazolone. The organic solvent can dissolve and stabilize 5-chloro-2-methyl-3-isothiazolone. A solvent having a hydroxy group such as glycol, alcohol and glycol ether can be used as the organic solvent. In certain system, an aliphatic or aromatic hydrocarbon can be used as the organic solvent. The organic solvent is preferably to ethylene glycol, propylene glycol, dipropylene glycol, ethylene glycol monomethyl ether, or ethylene glycol dimethyl ether.

An aqueous solution having a mixture of 5-chloro-2-methyl-3-isothiazolone and 2-methyl-3-isothiazolone can be used as the aqueous solution containing 5-chloro-2-methyl-3-isothiazolone. A ratio of 5-chloro-2-methyl-3-isothiazolone and 2-methyl-3-isothiazolone in the mixture is preferably to 50:50–99.99:0.01.

PREPARATION OF WATER FREE ISOTHIAZOLONE SOLUTION

Example 1

230 g isothiazolone hydrochloride salt (active component: 65%) having 5-chloro-2-methyl-3-isothiazolone (CMI) hydrochloride salt and 2-methyl-3-isothiazolone (MI) hydrochloride salt (in 3:1 weight ratio) was dispersed and dissolved in water to make 1000 g solution. 1000 g methylene chloride was added to the solution. A methylene chloride organic layer was taken out and evaporated. Ethylene glycol was added to the residue to thereby prepare a water free isothiazolone solution (10% concentration).

A CMI yield was 87%, MI yield was 27% and water content was 500 ppm (water content of ethylene glycol: 450 ppm).

Example 2

Example 1 was repeated except methylene chloride was replaced with chloroform.

A CMI yield was 85%, MI yield was 26% and water content was 500 ppm (water content of ethylene glycol: 450 ppm).

Example 3

Example 1 was repeated except methylene chloride was replaced with dichloroethane.

A CMI yield was 75%, MI yield was 20% and water content was 500 ppm (water content of ethylene glycol: 450 ppm).

Example 4

230 g isothiazolone hydrochloride salt (active component: 65%) having 5-chloro-2-methyl-3-isothiazolone (CMI) hydrochloride salt and 2-methyl-3-isothiazolone (MI) hydrochloride salt (in 3:1 weight ratio) and 300 g magnesium nitrate hexahydrate were dispersed and dissolved in water to make 1000 g solution. 1000 g methylene chloride was added to the solution. A methylene chloride organic layer was taken out and evaporated. Ethylene glycol was added to the residue to thereby prepare a water free isothiazolone solution (10% concentration).

A CMI yield was 86%, MI yield was 27% and water content was 500 ppm (water content of ethylene glycol: 450 ppm).

Example 5

Example 4 was repeated except methylene chloride was replaced with chloroform.

A CMI yield was 87%, MI yield was 27% and water content was 500 ppm (water content of ethylene glycol: 450 ppm).

Example 6

230 g isothiazolone hydrochloride salt (active component: 65%) having 5-chloro-2-methyl-3-isothiazolone (CMI) hydrochloride salt and 2-methyl-3-isothiazolone (MI) hydrochloride salt (in 3:1 weight ratio) and 300 g magnesium nitrate hexahydrate were dispersed and dissolved in water to make 1000 g solution. Magnesium oxide was added to the solution to control acidity of 1.5–4.0. 1000 g methylene chloride was added to the solution. A methylene chloride organic layer was taken out and evaporated. Ethylene glycol was added to the residue to thereby prepare a water free isothiazolone solution (10% concentration).

A CMI yield was 86%, MI yield was 27% and water content was 500 ppm (water content of ethylene glycol: 450 ppm).

Example 7

Example 6 was repeated except methylene chloride was replaced with nitromethane.

A CMI yield was 77%, MI yield was 23% and water content was 500 ppm (water content of ethylene glycol: 450 ppm).

Example 8

1000 g methylene chloride was added to a 1000 g commercial isothiazolone solution (product name: SKYBIO WG) having 5-chloro-2-methyl-3-isothiazolone (CMI) hydrochloride salt and 2-methyl-3-isothiazolone (MI) hydrochloride salt (in 10.3%:3.7% weight ratio). A methylene chloride organic layer was taken out and evaporated. Ethylene glycol was added to the residue to thereby prepare a water free isothiazolone solution (10% concentration).

A CMI yield was 87%, MI yield was 26% and water content was 500 ppm (water content of ethylene glycol: 450 ppm).

Comparative Example 1

230 g isothiazolone hydrochloride salt (active component: 65%) having 5-chloro-2-methyl-3-isothiazolone (CMI) hydrochloride salt and 2-methyl-3-isothiazolone (MI) hydrochloride salt (in 3:1 weight ratio) was dispersed and dissolved in ethyl acetate to make 1000 g solution. The solution was neutralized by using ammonia and then it was filtered. An ethyl acetate organic layer was taken out and evaporated. Ethylene glycol was added to the residue to thereby prepare a water free isothiazolone solution (10% concentration).

A CMI yield was 80%, MI yield was 80% and water content was 550 ppm (water content of ethylene glycol: 450 ppm).

Comparative Example 2

230 g isothiazolone hydrochloride salt (active component: 65%) having 5-chloro-2-methyl-3-isothiazolone (CMI) hydrochloride salt and 2-methyl-3-isothiazolone (MI) hydrochloride salt (in 3:1 weight ratio) was dispersed in ethyl acetate to make 1000 g solution. 70 wt % of ammonia required to neutralize the solution completely was added to the solution. And then, the solution was filtered. An ethyl acetate organic layer was taken out and evaporated. Ethylene glycol was added to the residue to thereby prepare a water free isothiazolone solution (10% concentration).

A CMI yield was 60%, MI yield was 20% and water content was 550 ppm (water content of ethylene glycol: 450 ppm).

Comparative Example 3

230 g isothiazolone hydrochloride salt (active component: 65%) having 5-chloro-2-methyl-3-isothiazolone (CMI) hydrochloride salt and 2-methyl-3-isothiazolone (MI) hydrochloride salt (in 3:1 weight ratio) was dispersed in ethyl acetate to make 1000 g solution. The solution was refluxed at 78–80° C. for 2 hr. At this time, a formed hydrogen chloride gas was caught by using sodium hydroxide solution. And then, the solution was cooled to room temperature and was filtered. An ethyl acetate organic layer was taken out and evaporated. Ethylene glycol was added to the residue to thereby prepare a water free isothiazolone solution (10% concentration).

A CMI yield was 60%, MI yield was 10% and water content was 600 ppm (water content of ethylene glycol: 450 ppm).

Water free isothiazolone solutions according to Examples 1–8 and Comparative examples 1–3 were incubated at 65° C. and then heat stabilities were measured by a high performance liquid chromatography. Table 2 shows the measured results.

TABLE 2

| | yield (%) | | water content (ppm) | | Stability (%) according to days | | | | | | | | |
|---|---|---|---|---|---|---|---|---|---|---|---|---|---|
| | CMI | MI | TS | EG | 0 | 2 | 4 | 6 | 8 | 10 | 12 | 14 | 16 |
| E 1 | 87 | 27 | 500 | 450 | 100 | 100 | 100 | 100 | 100 | 100 | 100 | 100 | 100 |
| E 2 | 85 | 26 | 500 | 450 | 100 | 100 | 100 | 100 | 100 | 100 | 100 | 50 | 0 |
| E 3 | 75 | 20 | 500 | 450 | 100 | 100 | 100 | 100 | 100 | 100 | 100 | 100 | 15 |
| E 4 | 86 | 27 | 500 | 450 | 100 | 100 | 100 | 100 | 100 | 100 | 100 | 10 | 0 |
| E 5 | 87 | 27 | 500 | 450 | 100 | 100 | 100 | 100 | 100 | 100 | 100 | 100 | 25 |
| E 6 | 86 | 27 | 500 | 450 | 100 | 100 | 100 | 100 | 100 | 100 | 100 | 100 | 15 |
| E 7 | 77 | 23 | 500 | 450 | 100 | 100 | 100 | 100 | 100 | 100 | 50 | 0 | 0 |
| E 8 | 87 | 26 | 500 | 450 | 100 | 100 | 100 | 100 | 100 | 100 | 100 | 100 | 100 |
| C 1 | 80 | 80 | 550 | 450 | 100 | 25 | 0 | 0 | 0 | 0 | 0 | 0 | 0 |
| C 2 | 60 | 20 | 550 | 450 | 100 | 100 | 100 | 15 | 0 | 0 | 0 | 0 | 0 |
| C 3 | 60 | 10 | 600 | 450 | 100 | 100 | 45 | 0 | 0 | 0 | 0 | 0 | 0 |

E: Example
C: Comparative example
CMI: 5-chloro-2-methyl-3-isothiazolone
MI: 2-methyl-3-isothiazolone
TS: Total solution
EG: Ethylene glycol

PREPARATION OF SUBSTANTIALLY PURE WATER FREE 5-CHLORO-2-METHYL-3-ISOTHIAZOLONE

Example 9

A 165 g mixture having 5-chloro-2-methyl-3-isothiazolone (CMI) hydrochloride salt and 2-methyl-3-isothiazolone (MI) hydrochloride salt (in 73%:27% weight ratio) was dispersed and dissolved in water to make 1000 g solution. 1000 g chloroform was added to the solution. A chloroform organic layer was washed out with water and evaporated. A 72 g mixture having CMI and MI (in 98.6%:1.4% weight ratio) was obtained.

Example 10

Example 9 was repeated except chloroform was replaced with methylene chloride and a 69 g mixture having CMI and MI (in 98.3%:1.7% weight ratio) was obtained.

Example 11

Example 9 was repeated except chloroform was replaced with 1,2-dichloroethane and a 65 g mixture having CMI and MI (in 98.1%:1.9% weight ratio) was obtained.

Example 12

Example 9 was repeated except chloroform was replaced with nitromethane and a 65 g mixture having CMI and MI (in 98.2%:1.8% weight ratio) was obtained.

Example 13

1000 g chloroform was added to a 1000 g commercial isothiazolone aqueous solution composition (14% concentration). A chloroform organic layer was washed out with water and evaporated. A 72 g mixture having CMI and MI (in 98.6%:1.4% weight ratio) was obtained.

PREPARATION OF SUBSTANTIALLY PURE WATER FREE 5-CHLORO-2-METHYL-3-ISOTHIAZOLONE HYDROCHLORIDE SALT

Example 14

165 g isothiazolone hydrochloride salt having 5-chloro-2-methyl-3-isothiazolone (CMI) hydrochloride salt and 2-methyl-3-isothiazolone (MI) hydrochloride salt (in 3:1 weight ratio) was dispersed and dissolved in water to make 1000 g solution. 1000 g chloroform was added to the solution. A chloroform organic layer was washed out with water and dried with anhydrous magnesium sulfate. And then, anhydrous magnesium was separated from the dried material. Hydrogen chloride gas was added to it. A 90 g mixture having CMI and MI (in 98.2%:1.8% weight ratio) was obtained by filtering the hydrogen gas added solids.

PREPARATION OF SUBSTANTIALLY PURE WATER FREE 5-CHLORO-2-METHYL-3-ISOTHIAZOLONE SOLUTION

Example 15

A water free isothiazolone solution (10% concentration) was prepared by adding ethylene glycol to the mixture having CMI and MI in 98.6%:1.4% weight ratio) according to Example 9. A water content of the water free isothiazolone solution was 500 ppm (water content of ethylene glycol: 450 ppm). The water free isothiazolone solution was incubated at 65° C. and then heat stabilities were measured by a high performance liquid chromatography. As a result, 100% active component of the water free isothiazolone solution was preserved for 10 days.

PREPARATION OF SUBSTANTIALLY PURE 5-CHLORO-2-METHYL-3-ISOTHIAZOLONE HYDROCHLORIDE SALT AQUEOUS SOLUTION

Example 16

130 g isothiazolone hydrochloride salt mixture according to Example 14 and 300 g magnesium nitrate hexahydrate were dispersed in water to make 1000 g solution. Anhydrous magnesium oxide was added to the solution to control pH 1.5–3.0. The solution was incubated at 65° C. and then heat stabilities were measured by a high performance liquid chromatography. As a result, more than 90% active component of the water free isothiazolone solution was preserved for 28 days.

Component ratio of isothiazolone obtained in Examples 9–14 is shown in Table 3.

TABLE 3

|  | CMI | MI |
| --- | --- | --- |
| Example 9 | 98.6% | 1.4% |
| Example 10 | 98.3% | 1.7% |
| Example 11 | 98.1% | 1.9% |
| Example 12 | 98.2% | 1.8% |
| Example 13 | 98.6% | 1.4% |
| Example 14 | 98.2% | 1.8% |

CMI: 5-chloro-2-methyl-3-isothiazolone
MI: 2-methyl-3-isothiazolone

The data in table 3 show that the isothiazolones according to Examples 9–14 are substantially pure.

Substantially pure water free 5-chloro-2-methyl-3-isothiazolone solution of Example 15 and substantially pure 5-chloro-2-methyl-3-isothiazolone hydrochloride salt aqueous solution of Example 16 had a high stability according to time.

Comparative Example 4

To a 500 ml jacketed flask equipped with an overhead agitator, thermometer, condenser fitted with a drying tube, and a temperature control bath, was added 50.6 g of a 73:27 mixture of CMI:MI and MI.HCl in 349.4 g of ethyl acetate. The slurry (10% solids) was heated to reflux and the solvent partially distilled (rate=20 ml/min) while replenishing the kettle with fresh ethyl acetate. Aliquots of the mother liquor were taken at various time points. These were filtered and the solids washed with ethyl acetate and analyzed for isothiazolone content. The filtrate from these aliquots were stripped and analyzed for the amount of free base isothiazolones. After 7 hours of refluxing, essentially all of the solids had dissolved. The reaction mixture was cooled to room temperature and then the solvent was stripped under reduced pressure. The results are shown in Table 4.

TABLE 4

| Time (hr) | filtrate (wt %) | | | solids (wt %) | | |
|---|---|---|---|---|---|---|
| | CMI | MI | CMI:MI | CMI.HCl | MI.HCl | CMI.HCl:MI.HCl |
| — | — | — | — | 53.9 | 18.0 | 73:27 |
| 0 | 86.9 | 1.2 | 98.6:1.4 | 37.2 | 32.4 | 53.4:46.6 |
| 1 | 90.0 | 2.8 | 97.0:3.0 | 0.31 | 64.7 | 0.5:99.5 |
| 2 | 82.0 | 10.8 | 88.4:11.6 | 0.29 | 65.1 | 0.4:99.6 |
| 3 | 77.2 | 14.6 | 83.9:16.1 | 0.42 | 65.2 | 0.6:99.4 |
| 4 | 76.5 | 18.2 | 80.5:19.5 | — | — | — |
| 5 | 72.8 | 20.0 | 78.4:21.6 | — | — | — |
| 6 | 73.6 | 20.8 | 78.0:22.0 | — | — | — |
| 7 | 69.4 | 25.7 | 73.0:27.0 | — | — | — |

CMI: 5-chloro-2-methyl-3-isothiazolone

MI: 2-methyl-3-isothiazolone

The data in table 3 and table 4 show that the isothiazolones according to Examples 9–14 are substantially pure compared to Comparative example 4.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A method of preparing water free isothiazolone comprising the steps of:

obtaining an extract from an aqueous solution containing isothiazolone by using a halogenationed hydrocarbon or nitrated hydrocarbon; and removing the halogenationed hydrocarbon or nitrated hydrocarbon from the extract.

2. The method of claim 1 further comprising a step of adding an organic solvent after the removing step.

3. The method of claim 2, wherein the organic solvent is selected from the group consisting of glycol, alcohol and glycol ether.

4. The method of claim 1, wherein the halogenationed hydrocarbon is selected from the group consisting of methylene chloride, chloroform, ethylene chloride and dichloroethane.

5. The method of claim 1, wherein the nitrated hydrocarbon is nitromethane or nitroethane.

6. The method of claim 1, wherein the isothiazolone is 5-chloro-2-methyl-3-isothiazolone and/or 2-methyl-3-isothiazolone.

7. A method of preparing substantially pure water free 5-chloro-2-methyl-3-isothiazolone comprising the steps of:

obtaining an extract from an aqueous solution containing 5-chloro-2-methyl-3-isothiazolone of formula 2 by using a halogenationed hydrocarbon or nitrated hydrocarbon;

washing the extract out with water; and removing the halogenationed hydrocarbon or nitrated hydrocarbon from the extract

[formula 2]

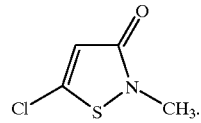

8. The method of claim 7, wherein the halogenationed hydrocarbon is selected from the group consisting of methylene chloride, chloroform, ethylene chloride and dichloroethane.

9. The method of claim 7, wherein the nitrated hydrocarbon is nitromethane or nitroethane.

10. The method of claim 7 further comprising a step of adding an organic solvent after the removing step.

11. A method of preparing substantially pure 5-chloro-2-methyl-3-isothiazolone hydrochloride salt comprising the steps of:

obtaining an extract from an aqueous solution containing 5-chloro-2-methyl-3-isothiazolone of formula 2by extracting with a halogenationed hydrocarbon or nitrated hydrocarbon;

washing the extract out with water;

adding hydrogen chloride gas to the extract; and filtering solids formed by the hydrogen chloride gass adding step

[formula 2]

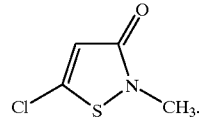

12. A method of claim 11, wherein the halogenationed hydrocarbon is selected from the group consisting of methylene chloride, chloroform, ethylene chloride and dichloroethane.

13. A method of claim 11, wherein the nitrated hydrocarbon is nitromethane or nitroethane.

* * * * *